United States Patent [19]
Martin

[11] Patent Number: 5,653,743
[45] Date of Patent: Aug. 5, 1997

[54] HYPOGASTRIC ARTERY BIFURCATION GRAFT AND METHOD OF IMPLANTATION

[76] Inventor: Eric C. Martin, 134 Old Post Road North, Croton on Hudson, N.Y. 10520

[21] Appl. No.: 304,043

[22] Filed: Sep. 9, 1994

[51] Int. Cl.⁶ ........................................... A61F 2/06
[52] U.S. Cl. .................. 623/1; 623/11; 606/153; 606/194
[58] Field of Search .................. 623/1-2, 11-12, 623/66; 606/108, 151, 153, 191, 194

[56] References Cited

U.S. PATENT DOCUMENTS

| | | |
|---|---|---|
| 3,657,744 | 4/1972 | Ersek . |
| 3,974,526 | 8/1976 | Dardik et al. .................. 623/1 |
| 4,140,126 | 2/1979 | Choudhury . |
| 4,501,263 | 2/1985 | Harbuck .................. 623/1 |
| 4,512,338 | 4/1985 | Balko et al. . |
| 4,577,631 | 3/1986 | Kreamer . |
| 4,778,467 | 10/1988 | Stensaas et al. .................. 606/152 |
| 4,787,899 | 11/1988 | Lazarus . |
| 5,104,399 | 4/1992 | Lazarus . |
| 5,292,331 | 3/1994 | Boneau .................. 623/1 |
| 5,360,443 | 11/1994 | Barone et al. .................. 612/1 |
| 5,387,235 | 2/1995 | Chuter .................. 623/1 |
| 5,489,295 | 2/1996 | Piplani et al. .................. 623/12 |
| 5,540,712 | 7/1996 | Kleshinski et al. .................. 623/1 |

OTHER PUBLICATIONS

*Transcatheter Cardiovascular Therapy*, in MedPRO Month, Sample Issue 1993, pp. 3-5.

*Primary Examiner*—John G. Weiss
*Assistant Examiner*—P. Zuttarelli
*Attorney, Agent, or Firm*—Fulbright & Jaworski LLP

[57] ABSTRACT

A small bifurcated graft is described which may be placed in each hypogastric artery to maintain patency both to it and to the external iliac artery and the leg below. The purpose is to maintain flow to the hypogastric artery while stenting the whole of the aorta-iliac system with endovascular overlapping straight tube grafts. Without this bifurcated device, aorto-iliac stenting would result in colonic ischemic.

11 Claims, 5 Drawing Sheets

HYPOGASTRIC ARTERY BIFURCATION GRAFT AND METHOD OF IMPLANTATION

BACKGROUND OF THE INVENTION

1. Field of the Invention

This invention relates to a percutaneous treatment for aorto-iliac disease, whereby the whole aorto-iliac segment is replaced by endovascular grafts without the requirement for open surgery.

2. Description of the Related Technology

The abdominal aorta and iliac vessels are subject to atherosclerotic disease whereby they become narrowed or occluded. Traditional repair has been an aorto-bifemoral graft which requires major surgery. According to this method, a Y-shaped graft is sutured end to side to the aorta below the renal arteries, and end to side in each femoral artery. After repair, while the disease segment is effectively bypassed, backflow will continue to perfuse the hypogastric artery and the inferior mesentery artery, if unobstructed. Angioplasty and stents have also been used to treat narrowed or occluded blood vessels, but their uses are limited to short lesions.

One of the major risks in aorto-iliac surgery is poor perfusion of the colon. If the aorto-iliac system is replaced with tube grafts, bowel ischemia will certainly occur in some patients as tube grafts would cover and bypass the hypogastric and/or inferior mesenteric arteries.

BRIEF DESCRIPTION OF THE INVENTION

The present invention provides a device for reconstructing the aorto-iliac segment which overcomes the disadvantages described above.

One object of the invention is to place, without open surgery, a bifurcated graft in each hypogastric artery. A further object of the invention is to provide endovascular grafts throughout the aorto-iliac system. A further object of the invention is to manage severe atherosclerotic aorto-ileac disease, either occlusive or non-occlusive, and at the same time, avoid the colonic ischemia which would result if prior art tube grafts were used.

Accordingly, there is provided according to the invention, a first graft which may be placed into the hypogastric artery, whereby additional contiguous tube grafts may then be used to reconstruct the remainder of the aorto-iliac segment in overlapping fashion. The invention features a Y-shaped graft, introduced from around the aortic bifurcation and placed in the hypogastric and external iliac artery from above. Tube grafts of varying sizes are then placed to reconstruct the remainder of the aorto-iliac segment.

There is also provided according to the invention a device for placing a bifurcated endovascular graft in each hypogastric artery without surgery so that the whole of the aorto-iliac segment may then have endovascular straight grafts placed as a means of managing atherosclerotic aorto-iliac disease.

There is further provided according to the invention a buttressed graft of material compatible with, and having extended life within, the vascular system. There is also provided according to the invention a bifurcation graft mounted on a stent so that the metal is covered and the inside smooth. The graft may have a pre-determined diameter and length. Furthermore, it may have a hole cut and marked so that it may be positioned across the external iliac artery and this hole will have a 1 cm tube of graft material attached.

There is also provided according to the invention a device for introducing the reinforcing device via the opposite femoral or ileac arteries which involves constraining the device on a catheter so that it is small enough to be introduced into the vascular system percutaneously. The graft, encased within a retractable membrane, is mounted on the head of a catheter. The catheter is introduced into either the femoral or iliac artery through a vascular sheath or surgical cut and is advanced around the aortic bifurcation. Under angiographic and fluoroscopic control, the catheter is positioned in the hypogastric artery. By partially withdrawing the retractable membrane, the upper portion of the graft is released. As it releases, it expands against the walls of the blood vessel. The remaining portion of the graft is then released into the blood vessel by fully withdrawing the retractable membrane. The catheter is then removed.

Another object of the present invention is to provide support to the bifurcated endovascular graft in order to prevent it from kinking or twisting once deployed. This is accomplished by bonding the graft to the inside of a self-expanding, mesh support tailored to the same measurements. The support may be a stent or a similar structure. Once the graft is deployed, the mesh provides the graft with the necessary support to prevent it from kinking or twisting.

Another object of the present invention is to prevent the formation of thrombi that may result from the prolonged exposure of blood to any metallic surface. This is accomplished by covering the mesh support with a suitable non-metallic material.

There is further provided a method of avoiding bowel ischemia by maintaining hypogastric artery patency by introducing endovascular grafts into the aorto-iliac segment.

DETAILED DESCRIPTION OF THE PREFERRED EMBODIMENT

Figure 1:
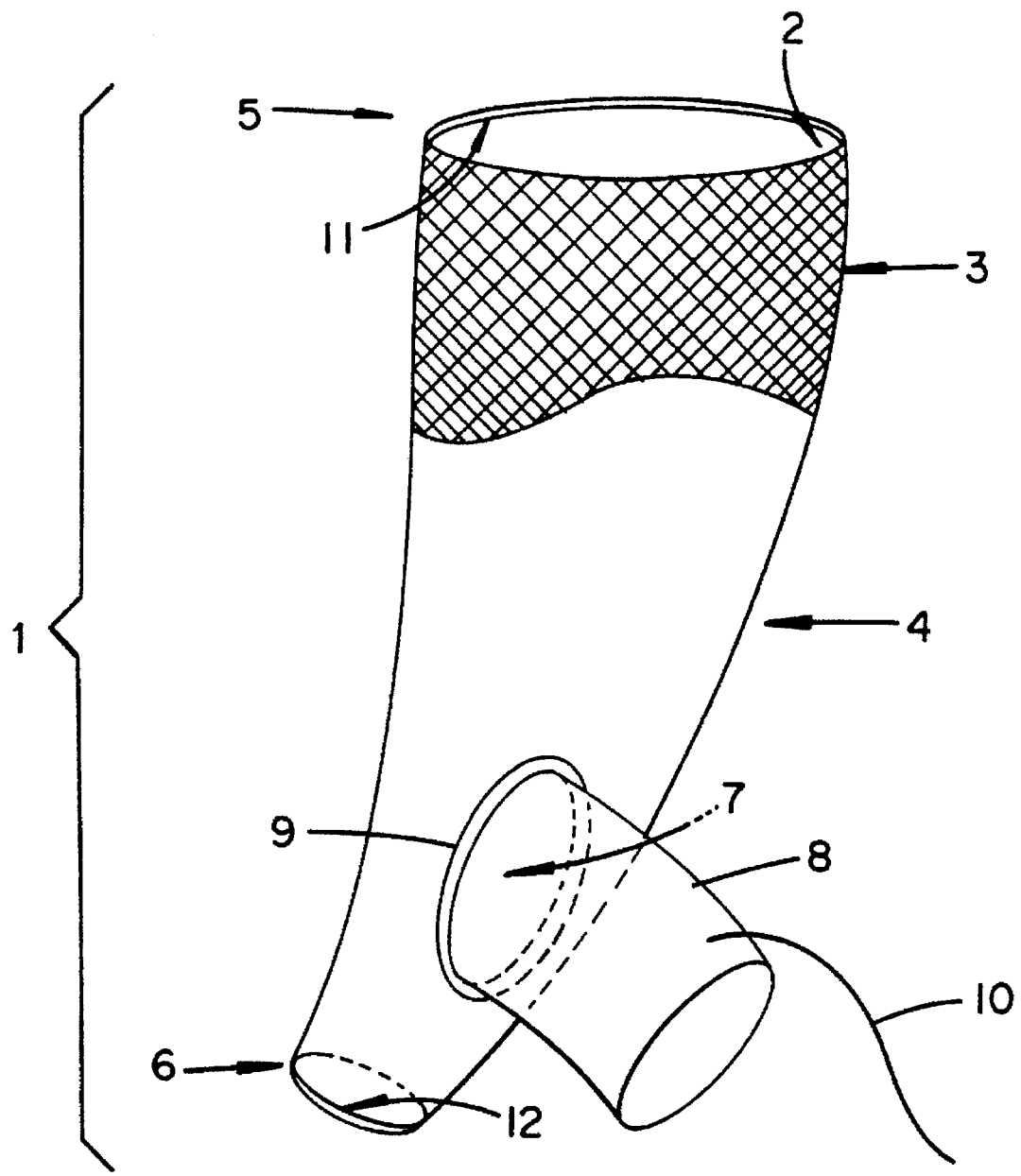
FIG. 1 shows an arterial prosthesis according to the instant invention.

Referring to FIG. 1, the prosthesis 1 of the instant invention consists of a graft 2, which may have a length of 4–5 cm. Examples of suitable materials include, but are not limited to, thin walled dacron or thin walled polytetrafluorethaline (PTFE). The whole of graft 2 may be bonded to a woven, stainless steel, self-expanding mesh support 3. The support may be a stent or a similar structure. The mesh support 3 may be of a medical grade super alloy stainless steel. The mesh support may optionally be covered on the outside by a non-metallic material or coating 4. Hereinafter, the graft 2/support 3 assembly will be referred to as "graft 2" for the sake of simplicity, unless otherwise indicated. According to a preferred embodiment, top end 5 of graft 2 has a diameter from 8–11 mm, which tapers over the length of graft 2 to bottom end 6 which has a diameter of 4–6 mm. According to particular embodiments of the invention, graft 2 tapers from 10 mm to 4 mm or from 8 mm to 3 mm. Graft 2 may exhibit an opening 7 having a diameter of 4 mm to 8 mm and located between 0.5 cm to 1.5 cm, preferably 1.0 cm, from the bottom end 6 of graft 2. A short tube graft 8, having a length of 0.5–1.5 cm, preferably 1.0 cm, may be attached at opening 7 to graft 2. Tube graft 8 may be unsupported, or alternatively, it may be bonded to a mesh support. According to one embodiment, tube graft 8 may be partially reinforced by a mesh support, for example, for the 0.5 cm which is proximal to graft 2.

According to a preferred embodiment, graft 2 may contain a platinum wire 9 around the perimeter of opening 7 so that opening 7 may be located and positioned by fluoroscopy. Alternatively, platinum wire 9 may be situated on the tube graft 8 close to the point where it meets graft 2. According to a further embodiment of the invention, a platinum wire 10 may be attached to the end of short tube graft 8. Platinum wire 10 may be used to assist in proper orientation of short tube graft 8 once graft 2 has been properly positioned in the vessel. According to a preferred embodiment, platinum wire 10 may have a length of approximately 3 cm. Metal Markers, such as platinum wires 11 and 12, may be placed at each end of graft 2 to allow its location to be tracked by fluoroscopy.

Figure 2:
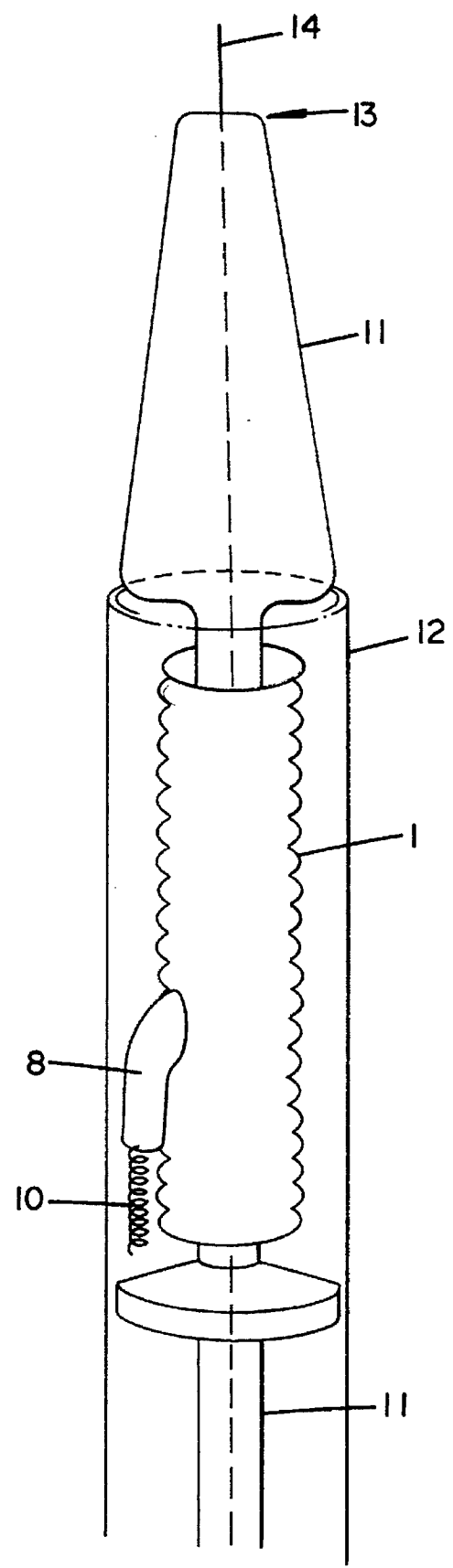
FIG. 2 shows an apparatus for introducing an arterial prosthesis into an arterial blood vessel.

An apparatus suitable for introducing and positioning prosthesis 1 into the aorto-iliac segment is shown in FIG. 2. According to a preferred embodiment, prosthesis 1 may be compressed and mounted on a catheter 11 and held in place by a retractable membrane 12. The short tube graft 8 may be folded around catheter 11 so that it faces away from tip 13 of catheter 11 with the platinum wire 10 coiled so that when introduced, it will hang free in the external ileac artery of the patient. According to a more preferred embodiment, catheter 11 may be tapered at one end 13 to an opening configured to receive guide wire 14. According to a preferred embodiment, guide wire 14 may have a diameter of 0.038 inches. Catheter 11 may have a shape adapted to prevent the collapsed support graft from sliding in either direction along catheter 11. A luer-lock hub may be located on the trailing end of the catheter.

Figure 3:
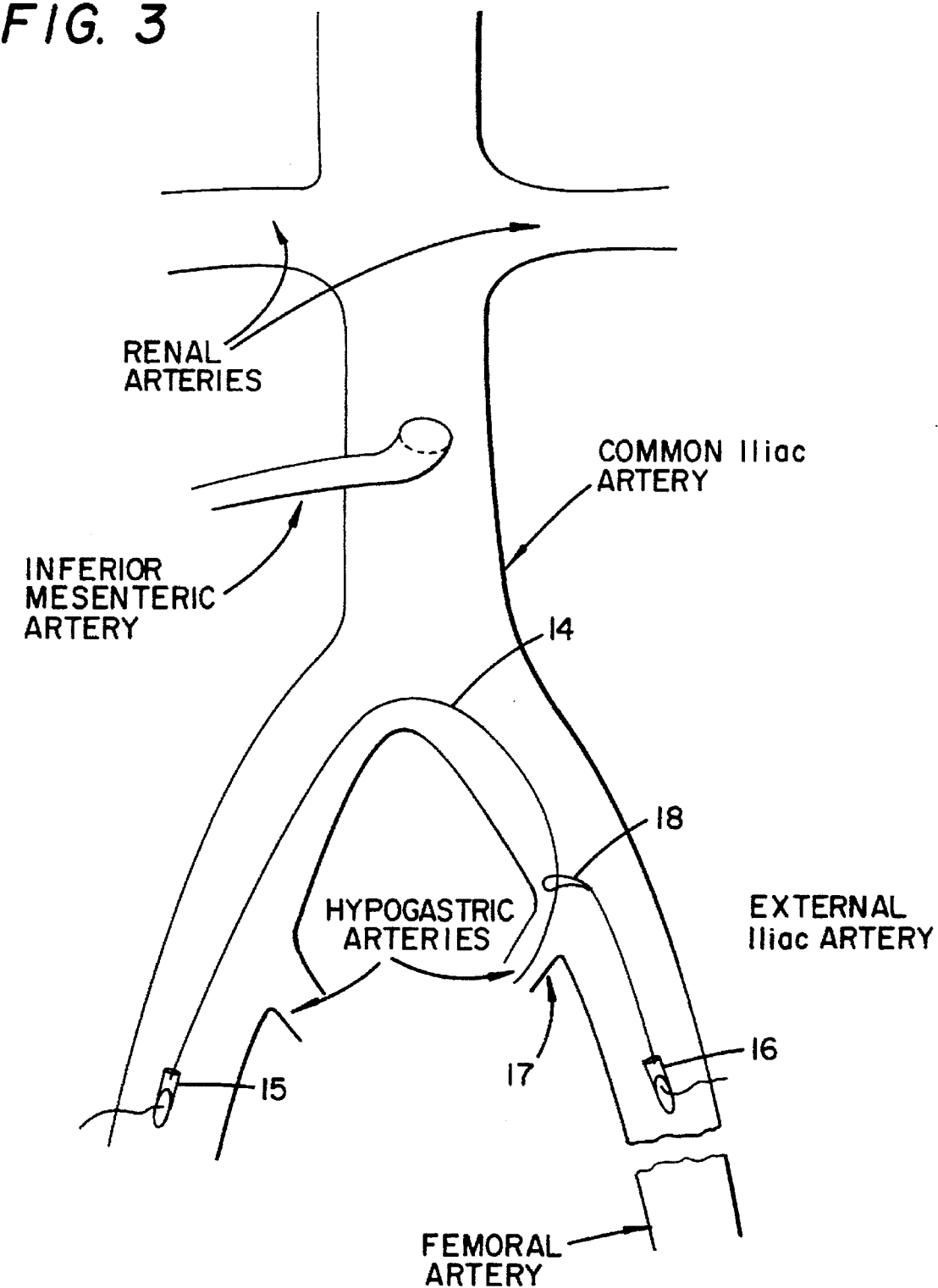
FIG. 3 is a representation of a method for introducing and placing an arterial prosthesis according to the invention.
Figure 4:
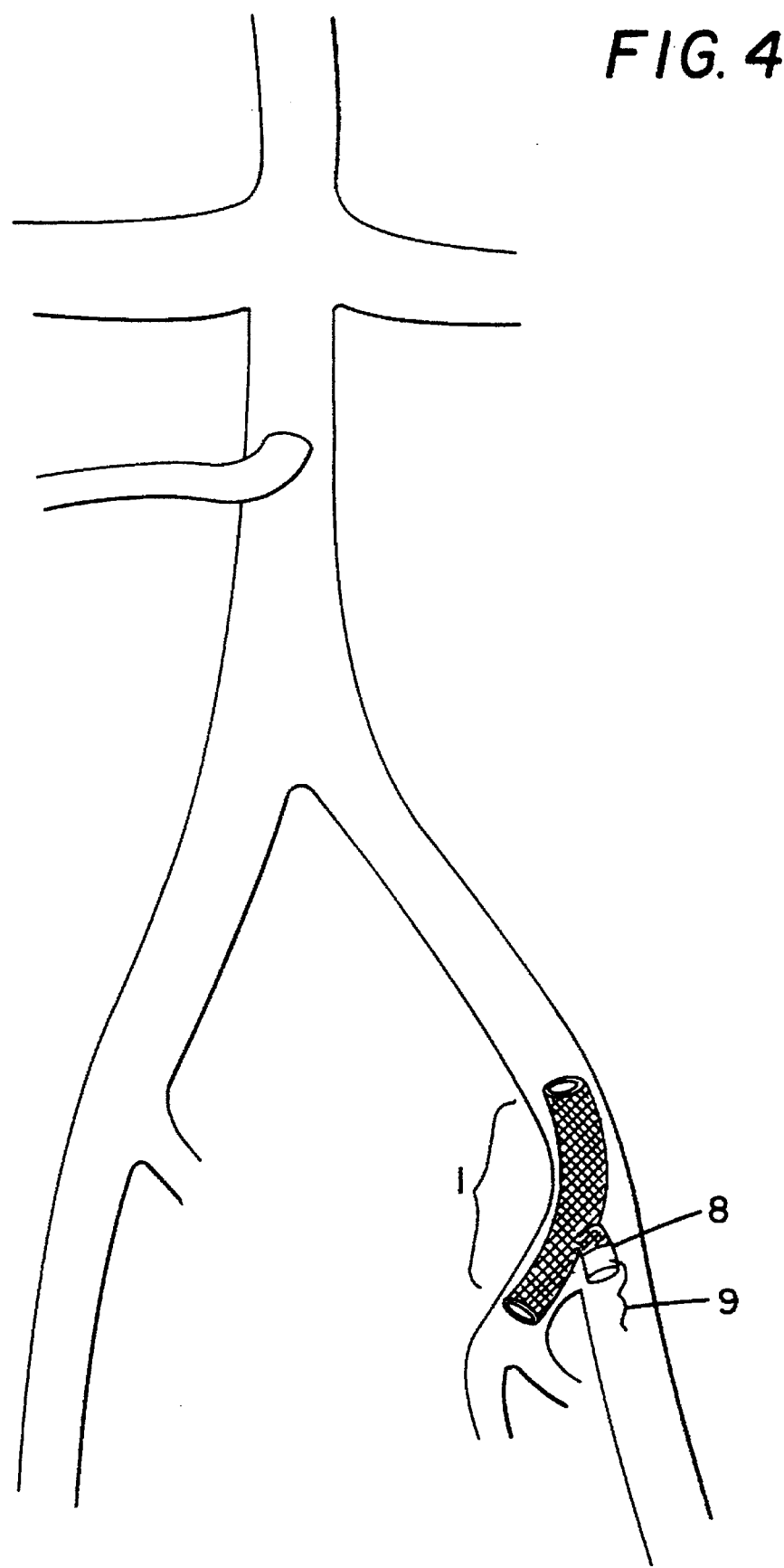
FIG. 4 shows a device according to the invention correctly positioned in the hypogastric artery.

Prosthesis 1 is introduced and positioned in the patient's body as illustrated in FIG. 3. Primary access is accomplished through a surgical cut or through a vascular sheath 15 placed percutaneously in the femoral artery or the ileac artery on the side opposite the target side. Alternatively, primary access may be established through the axillary artery in the patient's arm. A second access is established through a vascular sheath or cut down 16 in the femoral or ileac arteries on the target side. A no. 5 french catheter may optionally be introduced through the second access and positioned for angiographic control of the procedure. From the primary access, the hypogastric artery 17 on the target side of the body is catheterized around the aortic bifurcation, or from above via the aorta if an axillary artery access is used. Initial catheterization is performed using a locator catheter. Guide wire 14 is then threaded through the locator catheter until its end rests in the hypogastric artery. Locator catheter is then withdrawn and catheter 11, including prosthesis 1 mounted thereon and retained by retractable membrane 12, is introduced over guide wire 14 and positioned in the hypogastric artery 17 such that opening 7 and short tube graft 8 are correctly positioned across the external ileac artery. This may be done by fluoroscopically tracking the platinum wire 9. Optionally, a looped snare 18 may be introduced through the secondary access on the target side.

The snare may be used to hold guide wire 14 in place during the exchange between the locator catheter and catheter 11 and/or to assist in final placement of catheter 11 before prosthesis 1 is deployed.

Once catheter 11 is correctly positioned, membrane 11 is retracted and prosthesis 1 is thereby deployed and will expand under the force of the expandable support. Catheter 11 is then withdrawn. If necessary, balloon angioplasty may be performed to expand the graft/support assembly.

Through the secondary access, platinum wire 10 may then be seized and pulled down to correctly orient short tube graft 8. If necessary, the attached short tube graft 8 may then be smoothed into place with a balloon catheter introduced around the bifurcation. A straight tube graft 18 may then positioned to overlap the short tube graft 8 and to extend towards the common femoral artery, and angioplasty may then be undertaken to fully expand graft 18, if necessary. This process is then repeated from the grafted side to place a second prosthesis in the opposite hypogastric artery.

Figure 5:
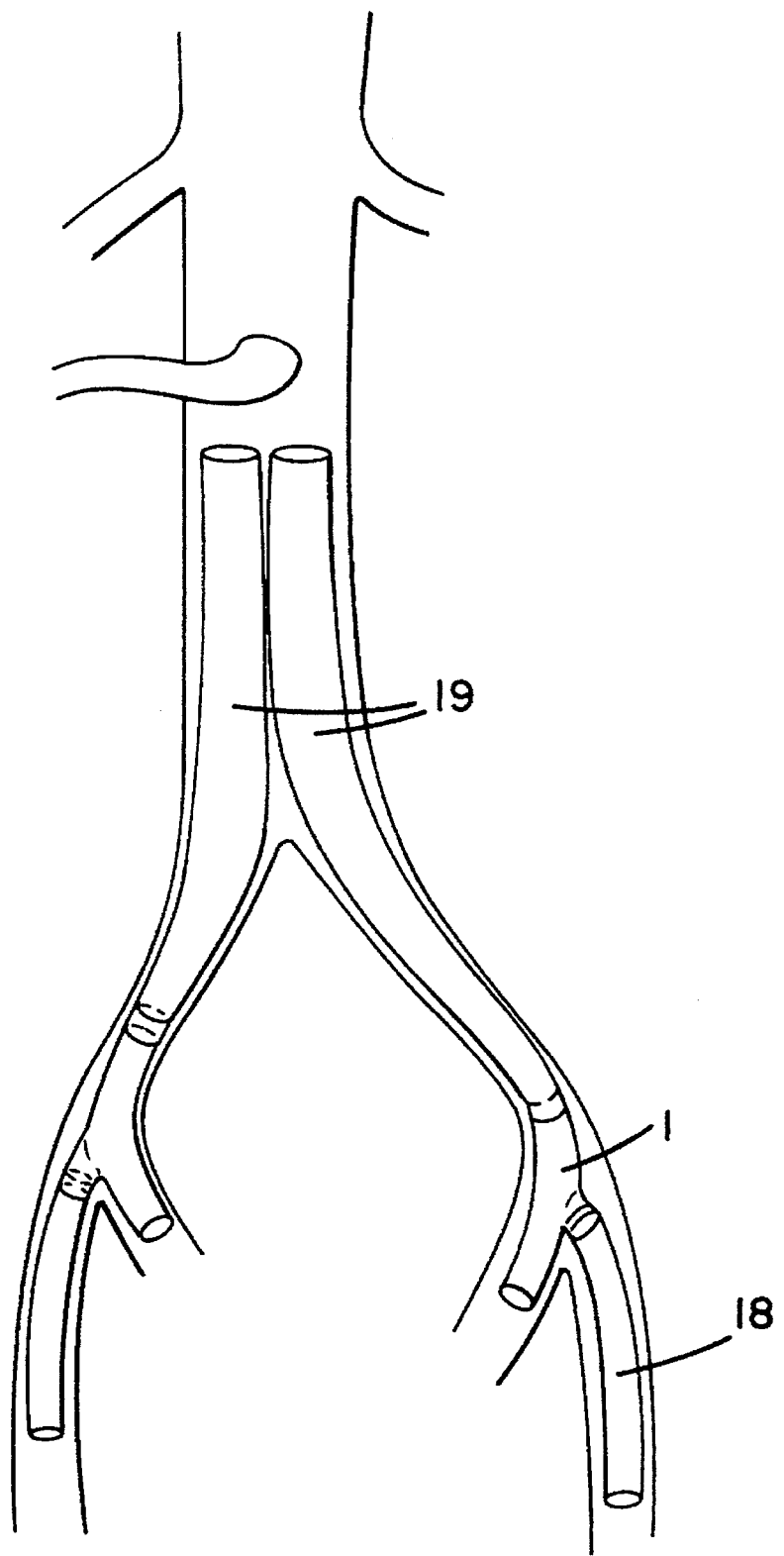
FIG. 5 is a representation of a final placement of an arterial prosthesis according to the invention and overlapping tube grafts.

If full aorto-ileac reconstruction is necessary, two tapered aortic tube grafts 19 may then be introduced and released simultaneously from each side to graft the aorta into each common iliac artery. The tube grafts may be released in such a manner that they overlap the common iliac artery segments of the hypogastric artery prostheses. If the inferior mesenteric artery is unobstructed and the infarenal aorta relatively normal, then the grafts may be positioned immediately below the inferior mesenteric artery as shown in FIG. 5. If the inferior mesenteric artery is occluded, or if there is more extensive disease in the aorta, parallel grafts may extend to just below the renal arteries. According to a most preferred embodiment, the diameters of the aortic tube grafts will be chosen such that the sum of their diameters is 20% greater than the aortic diameter.

I claim:

1. A bifurcated endovascular prosthesis comprising:
    a first tubular graft exhibiting a lateral opening;
    a compressible and self-expandable mesh support attached to substantially the entire outside surface of said first tubular graft, and
    a second tubular graft attached at one end to said lateral opening.

2. The bifurcated endovascular prosthesis according to claim 1, wherein said first and second grafts are made of a material selected from the group consisting of dacron and PTFE.

3. The bifurcated endovascular prosthesis according to claim 1, wherein the support comprises a metallic mesh.

4. The bifurcated endovascular prosthesis according to claim 1 further comprising a platinum wire situated around said opening.

5. The bifurcated endovascular prosthesis according to claim 1, wherein the length of said first graft is 4–5 centimeters.

6. The bifurcated endovascular prosthesis according to claim 1, wherein the length of said second graft is 0.5–1.5 centimeters.

7. The bifurcated endovascular prosthesis according to claim 1, wherein said first graft is tapered.

8. The bifurcated endovascular prosthesis according to claim 1, further comprising a wire extending from said second graft.

9. A method for the treatment of disease in an aorto-iliac segment compromising:

percutaneously introducing and placing a bifurcated arterial prosthesis into a hypogastric artery, and reconstructing contiguous portions of the aorto-iliac segment using percutaneously introduced tube grafts which are made to overlap in their final resting positions.

10. A method for introducing and positioning a bifurcated hypogastric arterial graft in a hypogastric artery comprising:

introducing a catheter containing said graft into the femoral artery opposite the target hypogastric artery;

feeding said catheter containing said graft around the aortic bifurcation;

positioning said catheter in a predetermined location within the hypogastric artery, and releasing said graft from said catheter.

11. The method according to claim 10, further comprising expanding said graft with balloon angioplasty.

* * * * *